United States Patent [19] … [11] Patent Number: 5,028,726
Farrell … [45] Date of Patent: Jul. 2, 1991

[54] PLATINUM AMINE SULFOXIDE COMPLEXES

[75] Inventor: Nicholas P. Farrell, Shelburne, Vt.

[73] Assignee: The University of Vermont and State Agricultural College, Burlington, Vt.

[21] Appl. No.: 476,235

[22] Filed: Feb. 7, 1990

[51] Int. Cl.$^5$ .................... C07F 15/00; A61K 33/00
[52] U.S. Cl. .................... 556/137; 556/136; 556/40; 514/492; 514/188; 546/2
[58] Field of Search ............. 556/137, 136, 40; 514/492, 188; 517/188; 546/2, 11

[56] References Cited

U.S. PATENT DOCUMENTS

| | | | |
|---|---|---|---|
| 4,336,148 | 6/1982 | Wirth et al. | 252/49.7 |
| 4,845,124 | 7/1989 | Kidani et al. | 514/492 |
| 4,861,905 | 8/1989 | Nowatari et al. | 556/40 |
| 4,882,447 | 11/1989 | Tsujihara et al. | 556/137 X |
| 4,886,894 | 12/1989 | Tsujihara et al. | 556/137 |

FOREIGN PATENT DOCUMENTS 55-144422 11/1980 Japan .

OTHER PUBLICATIONS

Farrell; Nicholas, "Dimethyl Sulphoxide as Leaving Group: Applications in Transition Metal Chemotherapy", *J. Chem. Soc., Chem. Commun.*, (1982), pp. 331–332.

Boucher, Heather and B. Bosnich, "Asymmetric Synthesis. Interligand Chiral Recognition between Prochiral Olefins and a Chiral Sulfoxide Coordinated to Platinum (II)", *Journal of the American Chemical Society*, vol. 99, No. 19 (Sep. 14, 1977), pp. 6253–6261.

Hacker, Miles P. et al. "Ascorbato(1,2-diaminocyclohexane):platinum(II) Complexes, a New Series of Water-soluble Antitumor Drugs", *Cancer Research*, vol. 45 (Oct. 1985), pp. 4748–4753.

Tobe, Martin L. and Abdul R. Khokhar, "Structure, Activity, Reactivity and Solubility Relationships of Platinum Diamine Complexes", *Wadley Medical Bulletin*, vol. 7, No. 1, pp. 114–137.

*Chem-Biol. Interactions*, vol. 11 (1975), p. 160.

*Primary Examiner*—Arthur C. Prescott
*Attorney, Agent, or Firm*—Armstrong, Nikaido, Marmelstein, Kubovcik & Murray

[57] ABSTRACT

Platinum amine sulfoxide complexes of the formula $[PtCl(diam)(R_2SO)]^+X^-$ wherein diam represents a bidentate amine, R is $C_3$–$C_7$ alkyl or cycloalkyl and $X^-$ is an anion, exhibit favorable anti-tumor activity in vivo against tumors susceptible to therapy with platinum.

14 Claims, No Drawings

PLATINUM AMINE SULFOXIDE COMPLEXES

BACKGROUND OF THE INVENTION

The clinical use of platinum complexes in cancer chemotherapy is now well established. The clinical utility of cisplatin, cis-[PtCl$_2$(NH$_3$)$_2$] or DDP, may be classified principally as curable (testicular cancer), sensitive (ovarian) and responsive (head and neck, small cell lung), and this spectrum of activity is matched by the "second-generation" analog carboplatin, [Pt(NH$_3$)$_2$(CBDCA)], where CBDCA=1,1'-cyclobutanedicarboxylate. The principal advantage of the latter complex is considered to be the reduction in the severe nephrotoxicity of the parent complex, the spectrum of activity being very similar, although this may eventually change.

The structure-activity relationships developed for platinum complexes has led to the development of a large number of complexes with antitumor activity. The basic adaptation of the parent molecule involved use of other amines besides NH$_3$ and modification of the leaving group by substitution of the chloride with other groups such as carboxylate, dicarboxylate or sulfate.

The potential for use of sulfur-bound dimethylsulfoxide (DMSO) as the leaving group in complexes of type cis-[Pt(am)$_2$(DMSO)$_2$]$^{2+}$ has been outlined by N. Farrell, "Platinum, Gold and Other Metal Chemotherapeutic Agents", ACS Symposium 209, 279 (1983) and N. Farrell, *J. Chem. Soc. (Chem. Comm.)* 1014 (1980). The rationale for these complexes is that despite the high trans influence of DMSO, which would be expected to labilize the group trans to it, the mutual labilization of the two DMSO ligands results in initial loss of DMSO to give aquo species, maintaining the cis-Pt(am)$_2$ moiety intact. Kinetic studies confirmed these observations; S. Lanza, D. Minnitti, R. Romeo, and M. L. Tobe, *Inorg. Chem.* 22, 2006 (1983). Further hydrolysis would give the active diaquo species:

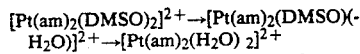
[Pt(am)$_2$(DMSO)$_2$]$^{2+}$→[Pt(am)$_2$(DMSO)(H$_2$O)]$^{2+}$→[Pt(am)$_2$(H$_2$O)$_2$]$^{2+}$ This series of bis(DMSO) complexes were not, however, active in vivo, due perhaps to the 2+ charge and lack of penetration into the cell. A further problem may be the rate at which the second sulfoxide ligand reacts, either to give the active diaquo species or in a direct reaction with DNA, the purported intracellular target of Pt complexes; A. L. Pinto and S. J. Lippard: *Biochem. Biophys. Acta* 780, 167 (1985). The series [Pt(am)$_2$(DMSO)Cl]$^+$ has been studied for their kinetic parameters and it is stated that this series is not antitumor active; A. R. Khokhar and M. L. Tobe, *J. Clin. Hematol. Oncol.* 7(1), 114 (1977).

Factors which limit more widespread clinical use of cisplatin are the development of drug resistance and dose-limiting toxicity such as nephrotoxicity. A number of bidentate amines, such as 1,2-diaminocyclohexane (dach) and 1,1'-bis(aminomethyl)cyclohexane (damch), give complexes which are non-cross-resistant with cisplatin. A limiting factor in development of dach and damch complexes has been both aqueous solubility and chemical stability. A recent approach to development of suitable, stable, water-soluble complexes, described in my copending application Ser. No. 180,956, filed Apr. 13, 1988, is the use of asymmetric sulfoxides in the general series of cationic complexes cis-[PtCl(am)$_2$(R'R"SO)]$^+$X$^-$, where (am)$_2$ represents two monodentate amines or a bidentate amine; R'R"SO is an asymmetric substituted sulfoxide and X$^-$ is a counteranion, usually nitrate. Such cationic sulfoxide complexes violate the previously understood and accepted structure-activity relationships for antitumor activity both because of their charge and the presence of the sulfur atom directly bound to platinum. The structure-activity relationships originally delineated for cisplatin stated unequivocally that a condition for good antitumor activity was that the complex must be neutral of form [Pt(amine)$_2$X$_2$], where X is a leaving group such as chloride, carboxylate, sulfate, etc.

SUMMARY OF THE INVENTION

We have now discovered that, contrary to what might be expected, non-asymmetric complexes of the formula

[PtCl(diam)(R$_2$SO)]$^+$X$^-$ wherein diam represents a bidentate amine and both R's are the same C$_3$-C$_7$ alkyl or cycloalkyl group, also exhibit greatly enhanced antitumor activity.

DETAILED DESCRIPTION OF THE INVENTION

As indicated above, the sulfoxide moieties which are present in the platinum amine sulfoxide complexes of the present invention are symmetrical sulfoxide moieties wherein R is C$_3$-C$_7$ alkyl or cycloalkyl. More specifically, R may be C$_3$-C$_7$ alkyl, straight-chain or branched, unsubstituted or substituted by C$_3$-C$_7$ cycloalkyl or C$_2$-C$_6$ alkenyl, or C$_3$-C$_7$ cycloalkyl. In addition, the two R's may be joined together to form the divalent alkylene group —(CH$_2$)$_n$— wherein n=3 to 7, with n=4 (tetramethylene) being preferred. Complexes wherein R is C$_4$ or C$_5$ alkyl, particularly n-propyl or n-butyl, are most preferred.

Since the sulfoxide group is neutral, complexes of the general formula [PtCl(diam)(R$_2$SO)]$^+$ are cationic, and an anion X is required to balance the charge on the complex. Any pharmaceutically acceptable anion is suitable for this purpose. Particularly preferred are Cl, Br, and No$_3$; weak nucleophiles such as HSO$_4$, H$_2$PO$_4$, BF$_4$ and PF$_6$; and carboxylates such as formate, acetate, benzoate, and the like. Nitrate is the anion most preferred.

A non-limiting list of bidentate amines (diam) which can be utilized in the platinum amine sulfoxide complexes of the present invention includes 1,2-diaminocyclohexane (dach), 1-amino-2-aminomethylcyclohexane (amch), 1,1'-bis(aminomethyl)cyclohexane (damch), 1-amino-2-aminomethyl-3,3,5-trimethylcyclohexane, 2-aminopyridine, 2-aminomethylpyridine, 2-aminopiperidine, 2-methylaminopiperidine, 1,2-diaminobenzene, wherein the benzene ring is unsubstituted or substituted by C$_1$-C$_6$ alkyl, C$_1$-C$_4$ alkoxy, halogen, hydroxy, C$_2$-C$_4$ alkenyl, carboxyl, C$_1$-C$_4$ alkyl ester, amino, C$_1$-C$_4$ alkylamino and di(C$_1$-C$_4$ alkyl)amino, ethylenediamine, 1,3-propanediamine, 2,2-diethyl-1,3-propanediamine and 1,2-diaminocycloheptane.

The synthetic scheme for preparing the complexes of the present invention utilizes the following sequence of reactions:

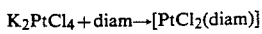
$$K_2PtCl_4 + diam \rightarrow [PtCl_2(diam)] \quad (1)$$

$$[PtCl_2(diam)] + R_2SO + AgNO_3 \rightarrow [PtCl(diam)(R_2SO)]^+NO_3^- \quad (2)$$

Displacement of chloride by sulfoxide in step (2) from the known complex prepared in step (1) gives the desired complex as its nitrate. The nitrate anion can be exchanged for by other anions using conventional procedures for effecting anion exchange.

The platinum complexes of the present invention may be administered to patients, including humans or animals, having tumors susceptible to platinum therapy, especially cisplatin and carboplatin therapy. Furthermore, since the compounds of the present invention are non-cross-resistant with cisplatin, the tumors which can be treated include tumors which are resistant to cisplatin and carboplatin therapy. The compounds may be administered in the form of sterile aqueous solutions, which are preferably administered intravenously or interarterially, although other forms of administration may be indicated in given cases.

Solutions for intravenous injections will normally be sterile physiological solutions. Suitable dosage forms can also include oily or aqueous injectable preparations, for intramuscular or intraperitoneal injection, syrups or the like liquid preparations, and solid dosage forms such as capsules, tablets and the like.

The effective amount of the complex of the present invention which should be administered to a patient can be determined by conventional methods which will be apparent to the skilled clinician. Normally, the activity of the platinum complex of the present invention will be evaluated in a screen along with the known complex such as cisplatin or carboplatin. The relative potency and the therapeutic index, i.e., the ratio of therapeutic effectiveness to toxicity, compared to that of the known analog will normally determine the relative dosage compared to the conventional doses of the analog for the type of malignancy being treated. Normally, however, from 1 to 500 mg/kg of the platinum complex will be administered to the patient in a given dose, with the dosage regime varying depending upon various factors which are well known to the skilled clinician.

At times it may be advantageous to administer the platinum complex of the present invention in combination with one or more agents that potentiate the tumor activity or mitigate any undesired side-effects of the platinum complex. For instance, the platinum complexes of the present invention may be administered together with reduced glutathione, as taught by U.S. Pat. application Ser. No. 105,169, filed 7 October 1987 now U.S. Pat. No. 4,871,528, the disclosure of which is hereby incorporated by reference.

It is recognized that certain of the platinum complexes having the formula shown above may have sufficiently high toxicity, or sufficiently low therapeutic indices, so as to be unsuitable for antitumor therapy in patients. However, these parameters can be readily determined by conventional screening tests, such as, for instance, with L-1210 murine leukemia cells implanted in mice, and such complexes should naturally be avoided.

The tumors in patients which are to be treated with the platinum complexes of the present invention are those tumors which are known to be susceptible to platinum therapy, such as tumors which are know to be treatable with cisplatin and carboplatin, as is well known to those in the art. It is known that cisplatin and carboplatin have been clinically used at the present to treat testicular, ovarian, bladder and head and neck cancers. It is also known that these agents have shown at least limited activity against non-small-cell lung cancer, osteogenic sarcoma, Hodgkins lymphoma, melanoma and breast cancer. Cisplatin has been found to be active against squamous cell carcinoma of the head and neck, squamous cell carcinoma of the cervix, oat cell or small cell anaplastic lung cancer, non-small-cell lung cancer (in combination with VP-16 or vinca alkaloids), adenocarcinoma of the stomach, carcinoma of the esophagus, adenocarcinoma of the prostate, osteogenic sarcoma, soft tissue and bone sarcomas, non-Hodgkins lymphoma, adenocarcinoma of the breast, brain tumors, thyroid cancer and endometrial cancer. All of the preceding tumors should respond to treatment with the platinum complexes of the present invention. The complexes of the present invention should also be active against certain tumors which are resistant to cisplatin, as is shown by animal studies conducted on the present complexes.

My invention is further illustrated by means of the following non-limiting examples:

EXAMPLE 1 cl Preparation of $[PtCl(damch)(n-Bu_2SO)]^+NO_3^-$

An equimolar amount of di-n-butyl sulfoxide (n-Bu$_2$SO) (1.06 g., 0.0065 mol) was added to a slurry of [PtCl$_2$(1,1-diaminomethylcyclohexane)](2.652 g., 0.0065 mol) in HPLC grade MeOH (30ml). To this was added 1 equivalent of AgNO$_3$ dissolved in hot MeOH. The reaction mixture was stirred overnight in the dark. The insoluble AgCl precipitate was filtered off and the filtrate rotoevaporated until the volume of methanol was approximately 2. ml. The concentrated solution was diluted with ether until a white solid just began forming. The flask was then placed in the freezer overnight and the resultant white crystals were filtered and washed with ether. A second recrystallization may be performed in the same manner. The complex was dried in vacuum over P$_2$O$_5$. Elemental analysis:

| Calculated: | % C, 32.2; | % H, 6.0, | % N, 7.0 |
| Found: | % C, 32.3; | % H, 5.7; | % N, 7.2 |

The corresponding n-propyl complex was prepared utilizing the procedure described above, but substituting di-n-propyl sulfoxide for di-n-butyl sulfoxide. Elemental analysis:

| Calculated: | % C, 29.6; | % H, 5.7; | % N, 7.4 |
| Found: | % C, 29.4; | % H, 5.4; | % N, 7.3 |

IR spectra were obtained as Kbr discs on Nicolet FT6000 series and Perkin-Elmer 1430 spectrophotometers. UV/Visible spectra were run on a Perkin-Elmer Lambda 4B instrument. NMR spectra were run on Bruker 250 and 270 MHz spectrometers. Pt NMR spectra (250 MHz) were run on D$_2$O with reference to a 0.1M Na$_2$PtCl$_6$ solution in D$_2$O as external reference. Samples were run using a pulse width of 15$\mu$s. Usually a sweep width of 30 KHz was used and 5000–10,000 scans were adequate. All shifts are positive to lower shielding. Spectral data for both complexes are given in Table 1.

TABLE 1

Characterization Data for [PtCl($R_2$SO)(diam)]$NO_3$

| R | IR(cm$^{-1}$)[a] (SO) | $^1$H and $^{195}$Pt NMR ($\delta$, ppm)[b] | | $\delta$(Pt) |
|---|---|---|---|---|
| | | $R_2$SO | diam[c] | |
| n-Pr | 1170,1125 | 3.5 (m) | 2.5–2.8 (m) | −3310 |
| | | 2.63 (m) | 1.1–1.4 (m) | |
| | | 1.21 (t) | | |
| n-Bu | 1120 | 3.6 (m) | 2.5–2.8 (m) | −3305 |
| | | 2.6 (m) | 1.1–1.4 (m) | |
| | | 1.6 (m) | | |
| | | 0.9 (m) | | |

[a] In KBr discs.
[b] In $D_2O$. Singlets except where indicated, d = doublet, m = multiplet. Numbers in parentheses in H NMR specctra refer to J(Pt-H) and are given only when observed clearly.
[c] All diamine peaks are multiplets centered at quoted values. Only one set is given for each example for clarity.

EXAMPLE 2

In Vitro Cytotoxicity Assay

L1210 murine leukemia cells sensitive to the cytotoxicity of DDP (L1210/0) were cultured as a suspension in McCoy's 5A medium supplemented with 5% donor horse serum and glutamine. L1210 cells, 40–60 fold resistant to DDP (L1210/DDP) or 30-fold resistant to [Pt(R,R-dach)$SO_4$] (L1210/dach), were cultured in McCoy's 5A medium supplemented with 10% fetal bovine serum and glutamine. Both cell lines were grown in a humidified atmosphere to 5% $CO_2$: 95% air at 37° C. For testing purposes, cells were diluted to $5 \times 10^4$ cells/ml and 1 ml of cell suspension aliquoted to disposable tissue culture tubes. Test compound was then added to the appropriate tubes (40 $\mu$l/tube) to attain final concentrations of 0.01, 0.1, 1.0 and 10 $\mu$g/ml. After 72 hours, the cell concentrations of all tubes were determined using a Coulter counter. The percent growth inhibition for each drug concentration was then calculated and the $ID_{50}$ (concentration of drug required to inhibit cell growth by 50%) was derived. The resistance factor for each compound was obtained by dividing the $ID_{50}$ (L1210/DDP) by the $ID_{50}$ (L1210/0). The results obtained, including a comparison with the corresponding methyl complex, are shown in Table 2.

TABLE 2

In Vitro Activity ($\mu$M) of [PtCl($R_2$SO)(damch)]$NO_3$ in L1210 Leukemia

| R | L1210/0 | L1210/DDP(R)[a] | L1210/dach(R) |
|---|---|---|---|
| Me | 1.09 | 3.90 (3.58) | — |
| Pr | 0.62 | 2.92 (4.70) | — |
| Bu | 0.39 | 2.36 (6.05) | 5.36 (41.23) |

[a] R = Resistance Factor which is defined as $ID_{50}$(Sensitive or L1210l0) divided by $ID_{50}$ (Resistant L1210/DDP or L1210/dach).

EXAMPLE 3

In Vivo Efficacy Studies

Male BDR mice weighing 18–20 gm were purchased from the National Cancer Institute and housed in an environment having controlled humidity, temperature and photoperiods. The animals had food and water available ad libitum and wood chip bedding was changed daily. The L1210/0 and P388 murine leukemias were maintained as ascites tumors by weekly intraperitoneal (i.p.) inoculations of $10^6$ cells For testing purposes, $10^6$ tumor cells were inoculated i.p. (day 0) and mice were administered test compound i.p. on days 1, 5 and 9. Animals were observed daily for signs of toxicity and deaths and the day of death recorded for each animal that died during the 60 day observation period. The efficacy of each dose of compound tested was evaluated by calculating the percent increased life span determined by dividing the mean survival time of treated mice (using the day of death of only those animals that dies during the 60 day period) by the mean survival time of non-treated tumor bearing control animals (% T/C). Compounds exhibiting a % T/C > 140 are considered to have significant antitumor activity. An additional index of antitumor activity is the number of long term survivors defined as treated animals alive at the end of the study. The complexes tested and the results observed are summarized in Table 3 (L1210 leukemia) and in Table 4 (P338 leukemia). The data in Table 5 compares to the in vivo activity of [PtCl(n-$Bu_2$SO)](damch)$NO_3$ with that of cisplatin.

TABLE 3

Antitumor Activity of [PtCl($R_2$SO)(damch)]$NO_3$ in L1210 Leukemia in vivo

| R | | Dose mg/kg | % T/C |
|---|---|---|---|
| Me | damch | 3 × 100 | 152 |
| n-Pr | damch | 3 × 25 | 185 |
| | | 3 × 12.5 | 162 |
| n-Bu | damch | 3 × 25 (D5W) | 260 |

TABLE 4

Antitumor Activity of [PtCl($R_2$SO)(damch)]$NO_3$ in P388 Leukemia in vivo

| R | Dose | % T/C |
|---|---|---|
| n-$Bu_2$SO | 3 × 25 | 189 |
| | 3 × 25 (D5W) | 195 |
| | 3 × 12.5 | 146 |
| | 3 × 6.25 | 167 |

TABLE 5

Antitumor Activity of [PtCl(n-$Bu_2$SO)(damch)]$NO_3$ as Compared to Cisplatin in B16 Melanoma in vivo

| | | Dose | % T/C |
|---|---|---|---|
| n-$Bu_2$SO | complex | 3 × 25 | 188 |
| | | 3 × 12.5 | 136 (1/6) |
| | | 3 × 6.25 | 154 |
| Cisplatin | | 3 × 5 | 170 |

Complex dissolved in saline. Tumor administered subcutaneously (s.c.), drug administered intraperitoneally (i.p.).

It is apparent from the test results summarized in Tables 2–5 that the platinum amine sulfoxide complexes of the present invention exhibit significant antitumor activity at 25 mg dosage levels, and, in general, do not exhibit cross-resistance to cisplatin. It is unexpected, considering the increase in lipophilicity due to presence of additional carbon atom, that the $C_3$-$C_7$ alkyl and cycloalkyl complexes of the present invention both possess adequate solubility in water and exhibit greatly enhanced antitumor activity as compared to complexes wherein the sulfoxide is dimethyl sulfoxide.

What is claimed is:

1. A platinum amine sulfoxide complex of the formula

[PtCl(diam)($R_2$SO)]$^+$X$^-$ wherein R is $C_3$-$C_7$ alkyl optionally substituted by $C_3$-$C_7$ cycloalkyl or $C_2$-$C_6$ alkenyl, or $C_3$-$C_7$ cycloalkyl, diam is a bidentate amine and X$^-$ is a pharmaceutically acceptable anion.

2. A platinum amine sulfoxide complex according to claim 1, wherein R is $C_3$-$C_7$ alkyl.

3. A platinum amine sulfoxide complex according to claim 2, wherein R is n-propyl or n-butyl.

4. A platinum amine sulfoxide complex according to claim 3, where R is n-butyl.

5. A platinum amine sulfoxide complex according to claim 3, wherein R is n-propyl.

6. A platinum amine sulfoxide complex according to claim 1, wherein diam is 1,2-diaminocyclohexane, 1-amino-2-aminomethylcyclohexane, 1-1$^1$-bis(aminomethyl)cyclohexane, 2-aminopyridine, 1,2-diaminobenzene or a $C_{1-4}$ alkylene diamine.

7. An platinum amine sulfoxide complex according to claim 6, wherein the diamine is 1,2-diaminocyclohexane or 1,1$^1$-bis(aminomethyl)cyclohexane.

8. A platinum amine sulfoxide complex according to claim 1, wherein X is Cl, Br or $NO_3$.

9. A platinum amine sulfoxide complex according to claim 8, wherein X is $NO_3$.

10. A platinum amine sulfoxide complex according to claim 1, wherein R is n-propyl, diam is 1,1$^1$-bis-(aminomethyl) cyclohexane and X$^-$is $NO_3$.

11. A platinum amine sulfoxide complex according to claim 1, where R is n-butyl, diam is 1,1'-bis(aminomethyl)cyclohexane and X$^-$is $NO_3$.

12. An antitumor composition comprising an antitumor effective amount of a platinum amine sulfoxide complex according to claim 1 in combination with a pharmaceutically acceptable carrier.

13. An antitumor composition according to claim 12 containing 1–500 mg of the platinum amine sulfoxide complex.

14. A method of treating an animal having a tumor susceptible to therapy with platinum which comprises administering to said animal an antitumor effective amount of a platinum amine sulfoxide complex according to claim 1.

* * * * *